United States Patent [19]

Metzner et al.

[11] 4,041,176

[45] Aug. 9, 1977

[54] PRESERVATIVE COMPOSITION FOR WOOD AND WOOD BUILDING MATERIALS AND METHOD OF USING SAME

[75] Inventors: Wolfgang Metzner, Krefeld; Hubert Koddebusch, Moers, both of Germany

[73] Assignee: Desowag-Bayer Holzschutz GmbH, Duesseldorf, Germany

[21] Appl. No.: 602,903

[22] Filed: Aug. 7, 1975

[30] Foreign Application Priority Data

Aug. 9, 1974 Germany ............................ 2438334

[51] Int. Cl.² .............................................. A01N 9/24
[52] U.S. Cl. .................................. 424/318; 424/217; 424/230; 424/317; 424/347; 424/352; 424/353
[58] Field of Search ............... 424/353, 317, 318, 347, 424/352, 217, 230

[56] References Cited

PUBLICATIONS

Chemical Abstracts, vol. 78 (1973), pp. 112860x, 93456b.
Chemical Abstracts, vol. 77 (1972), p. 110398h.
Chemical Abstracts, vol. 79 (1973), p. 20478w.
Chemical Abstracts, vol. 66 (1967), p. 117625m.

*Primary Examiner*—V. D. Turner
*Attorney, Agent, or Firm*—Bacon & Thomas

[57] ABSTRACT

Disclosed is a preservative composition for wood and wood construction material, comprising an organic solvent base, preferably an oily or oil-like solvent, at least one insecticide, organic fungicide or wood-preserving organic chemical compound which is soluble in the solvent, and typically from about 0.005 to 0.1% by weight, and more preferably between about 0.01 and 0.03% by weight, of at least one organic lithium compound soluble in the solvent, preferably lithium naphthenate or lithium octoate. The lithium compound provides also a marking effect for the compositions during application and subsequent thereto.

29 Claims, No Drawings

PRESERVATIVE COMPOSITION FOR WOOD AND WOOD BUILDING MATERIALS AND METHOD OF USING SAME

BACKGROUND OF THE INVENTION

The present invention pertains to a preservative composition for wood and wood building materials, and more especially, to such a preservative composition based upon an organic, preferably an oily or oil-type solvent material and one or more organic insecticides and/or fungicides and/or wood-preserving organic chemcial compounds which are soluble in the solvent. The invention particularly concerns wood preservatives having a marking effect, and the invention further pertains to a process for the preparation of such marking and/or marked wood preservatives as well as to a method for using such preservatives.

It is already known to mark oily and oil-like wood preservative compositions with oil-soluble cadmium compounds, particularly to provide qualitative detection and to determine the amount of preservative in the wood (see German Pat. No. 1,080,327). For this purpose there are used as oil soluble cadmium compounds the salts of acids present in tall oil or salts of naphthenic acids. The additive component must be utilized in amounts of approximately 0.05% by weight. Based upon hygienic reasons, however, as a result of their toxicity, cadmium compounds should no longer be contained in oily wood preservative compositions. In addition, cadmium compounds are not universally usable in mineral oil-containing wood preservative compositions. They are soluble only in hydrophilic solvents, which can be used not at all or only in small amounts for wood preservative compositions.

Consideration has also been given to marking the preservative composition with weakly radioactive substances, although such a solution appears objectionable based on hygienic considerations as a result of the only difficultly ascertainable, possible danger to people or animals, especially in the case of unforeseeable accumulation of the marking material.

Attempts have also been made to use fluorescing compounds, such as pyrene and fluoranthene as marking substances in oily compositions. In the periodical "Der praktische Schaedlingsbekaempher", from January 1974, pages 1-4 (Vol. 26), a report about a new process for analyzing oily wood preserving materials with the use of fluorescing compounds as the marking substance is presented by Dr.-Ing. H.-J. Petrowitz and Ing. grad. W. Berghoff. According to this analysis method, however, approximately 2% pyrene or fluoranthene are required in the composition, in order to enable determination of the amount of wood preservative in the wood, so that the relatively high weight amounts and the costs connected therewith place in question the practical application of this method. Moreover, these compounds are not totally without objection from the standpoint of health and/or hygiene.

Purely organic marking substances such as those mentioned hereinabove, have the disadvantage that even at room temperature a certain vapor pressure results and that, as a result of this fact, a considerable portion of the marking substance evaporates over the years.

SUMMARY OF THE INVENTION

It is therefore an object of the present invention to provide an improved wood preservative composition and method of preparing and using same.

A further object of the present invention resides in the provision of an improved process for marking wood preservative compositions containing organic solvents, preferably for the marking of oily or oil-type wood preservative compositions.

It is also an object of the present invention to provide a wood preserving composition which does not possess the disadvantages discussed hereinabove and which is suitable for readily providing qualitative evidence and/or a quantitative determination of treatment of wood products.

A further object of the present invention resides in the provision of a wood preservative composition wherein the marking substance therefor can be effectively employed in only very small amounts.

It is another object of the invention to provide a wood preserving composition and method which are completely unobjectionable from a hygienic standpoint.

Yet another object of the present invention resides in the provision of a wood preservative composition wherein the marking material remains dissolved in the oily or oil-like solvent over long periods of time and under unsatisfactory storage conditions.

Another object of the invention resides in the provision of a wood preservative composition wherein the marking substance is to a certain extent resistant to evaporation after application of the preservative.

In accomplishing these and other objects, there has been provided in accordance with the present invention a preservative composition for wood and wood construction material, comprising an organic solvent base, preferably of the oily or oil-like type, at least one insecticide, organic fungicide or wood-preserving organic chemical compound which is soluble in the solvent, and as a specific improvement to the composition, at least one organic lithium compound which is soluble in the solvent. Preferably the organic lithium compound is present in an amount between about 0.005 and 0.1% by weight, calculated as metallic lithium and based upon the total composition, and more preferably between about 0.01 and 0.03% by weight. Preferred organic lithium compounds are lithium naphthenate and lithium octoate.

In another aspect of the present invention, there has been provided a process for producing a marking or marked preservative composition for wood and wood construction material, comprising the step of mixing at least one insecticide, organic fungicide or wood-preserving organic chemical compound with an organic solvent base, preferably an oily or oil-like base, and adding to the composition between about 0.005 and 0.05% by weight of at least one organic lithium compound which is soluble in the solvent. Preferably the lithium compound is first mixed with a minor amount of the solvent and is subsequently added to the composition in a pasty or dispersed condition or in the form of a solution.

In yet another aspect of the invention, there has been provided a method of treating wood and wood construction material with a wood preservative composition, comprising applying to the wood a composition as defined hereinabove, whereby there is provided a marking effect on the treated wood, to provide qualitative evidence of treatment, to provide a quantitative determination or to determine the amount of preservative in the wood.

Other objects, features and advantages of the present invention will become apparent from the detailed description of preferred embodiments which follows.

DETAILED DESCRIPTION OF PREFERRED EMBODIMENTS

In accordance with a preferred embodiment, a wood preservative composition has been discovered in connection with which the marking substance itself can serve as an active ingredient. Furthermore, the wood preserving composition possesses advantageous preservative properties, is easily preparable and is qualitatively and/or quantitatively determinable with respect to the marking substance, even after application.

It has been surprisingly determined that all of the foregoing requirements are met with a wood preserving composition based upon an organic, preferably oil-like or oily solvent and one or more organic insecticides and/or organic fungicides or wood preserving organic chemical compositions, which are soluble in the solvent, when the composition contains additionally one or more organic, oil-soluble lithium compounds as a marking component and/or as an active ingredient.

There may be employed as the organic, oil-soluble lithium compounds the well known, conventional lithium compounds such as lithium naphthenate, lithium octoate, lithium acetate, lithium citrate, lithium glycerophosphate, lithium fumarate, lithium salicylate and lithium benzoate. In accordance with an advantageous embodiment of the invention, there is employed as the organic lithium compound lithium naphthenate and/or lithium octoate.

The lithium compounds are not contained in the conventional raw materials which are employed for the preparation of wood preservative compositions, nor are they contained in wood and wood building products in amounts which would interfere with the detection function. In addition, organic lithium compounds, e.g., lithium naphthenate, dissolve without dissolving intermediary in oily and oil-type wood preservatives which contain monochloronaphthalene, fuel oil, white spirits and/or aliphatic and aromatic hydrocarbons and the like as solvents. As oily or oil-like organic solvents, there are employed such solvents having an evaporation number greater than 35 referred to diethylether and a flame point above 35, preferably above 55., according to DIN 51 755.

In the case of an organic, oil soluble lithium compound which is contained in wood preservative compositions in an amount of 0.02% by weight, calculated on the metal, after a storage time of 1 year at 40° C. the lithium was fully recovered from the treated wood by means of quantitative analysis. To carry out this test, the wood sample to be tested for the wood preservative composition is digested with a mixture of nitric acid and perchloric acid and subsequently the lithium quantitatively determined by atom absorption spectrometry.

In the case that the organic, oil-soluble lithium compound is to be employed as an active ingredient having a wood preservative effect in addition to the marking function, in general, additive amounts of more than 0.1% by weight, preferably 0.3 to 2% by weight of the lithium compound employed (calculated as metal and based upon the preservative composition) are required. To render the wood preserving composition suitable for marking, amounts of organic, oil-soluble lithium compounds of from 0.005 to 0.1% by weight, preferably from 0.01 to 0.03% by weight (calculated as metal and based upon the wood preservative composition) are sufficient for a marking effect of the wood preservative compositions and also the wood and wood construction materials treated therewith.

In accordance with an advantages embodiment of the present invention, the wood preserving composition is comprised of a mixture of one or more organic non-volatile solvents having an evaporation number greater than 35 referred to diethylether and a flame point greater than 35, preferably greater than 55, according to DIN 51 755 in an amount of more than 30% by weight, more preferably above 50% by weight, and from 0.5 to 20% by weight, preferably 2 to 10% by weight of one or more organic chemical insecticides and/or organic chemical fungicides or wood preserving organic chemical compounds which are soluble in the organic, non-volatile solvent, as well as from about 0.005 to 0.1, preferably from about 0.01 to 0.03% by weight of an organic and oil soluble lithium compound (calculated as metal and based on the wood preservative composition), preferably lithium naphthenate and/or lithium octoate, as well as from 0 to 10% by weight of a plasticizer and/or fixer and/or a more volatile solvent.

As organic non-volatile solvents having an evaporation number above 35 referred to diethylether and a flame point greater than 35, preferably greater than 55 according to DIN 51 755, there are employed the well known organic non-volatile solvents, preferably oily or oil-like solvents, such as mineral oils having a boiling range of between about 170° and 220° C., white spirits having a boiling range of from about 170° to 220° C., spindle oil having a boiling range of from about 250° to 350° C., kerosene, aromatics having the boiling range of from about 160° to 280° C., oils of turpentine and the like.

In accordance with an advantageous embodiment of the invention, the wood preserving composition contains in addition from about 1 to 20% by weight, preferably from about 4 to 15% by weight of a binder. In a suitable embodiment, a synthetic resin is employed as the binder in the form of an emulsion, dispersion or solution, preferably an alkyd resin or a modified alkyd resin or a phenolic resin or an indene-cumarone resin. Bitumens or bituminous substances can also be utilized as the binder. In addition, there may be included in the compositions of the invention the well known dyes, pigments, water repellants, deodorants and inhibitors or corrosion protectors and the like. Paraffins, waxes, wool grease and the like in amounts of between about 0.5 to 5% by weight, preferably from about 2 to 3% by weight, based on the wood preserving composition, are employed as water repellant materials.

The following materials may be employed as fixers or plasticizers:

a. Plasticizers, for example, alkyl, aryl or aralkyl phthalates, preferably dibutyl, dioctyl and benzylbutylphthalate, alkyl phosphate, preferably tributyl phosphate, adipates, preferably di(2-ethylhexyl) adipate, stearates and oleates, for example, alkyl stearates or alkyl oleates, preferably butyl oleate, butyl stearate or amyl stearate, bis-(dimethylbenzyl)ether, para-toluene sulfonic acid ethyl ester, and the like;

b. Oils, for example, linseed oil, castor oil, tall oil and their esters; or c. Other fixers, such as ketones having alkyl, aryl or arylalkyl groups, preferably benzophenone, ethylbenzophenone; polyvinyl alkyl esters, preferably polyvinyl methyl ether.

The well known and conventional organic insecticides and/or organic fungicides or wood-preserving organic chemical compounds are employed as the insecticide, fungicide or wood preserving components of the compositions according to the present invention. Preferably, there are employed thio phosphoric acid esters, carbamates, pentachlorophenol, monochloronaphthalene and Lindane, (α hexachlorocyclohexane). Under the term organic chemical compounds, it is intended also that metal-organic compounds be included within the scope of the invention.

The invention furthermore pertains to a process for the preparation of the making or marked wood preserving compositions by the addition of the organic oil soluble lithium compound in an amount of from about 0.005 to 0,1.% by weight, preferably from about 0.01 to 0.3% by weight (Calculated as metal and based on the wood preserving composition). Thus, an exactly determined amount of this organic, oil-soluble lithium compound is mixed to the wood preserving composition, and preferably, lithium naphthenate or lithium octoate is employed for this purpose. The organic and/or oil-soluble lithium compound or a mixture thereof is mixed with oil or oil-like organic solvent prior to its addition to the wood preservative composition or the remaining components of a wood preservative composition. Thus, the lithium compound is converted into a paste-formed or dispersed condition, or into a solution.

The wood preservative composition or marking composition, or the marking process serves therefore for an effective marking of the wood or wood construction materials treated with the wood preservative compositions, in particular for qualitative indication, for quantitative determination or for determination of the amount of treating composition in the woods. When the process for marking of oily and oil-like wood preservative compositions is carried out, it is a pre-requirement that the wood preservative in all of its types wherein applied as a preservative or abating wood preservative, e.g., as wood protective oils, wood protective base coatings, wood protective glazes or dispersions or other wood protecting coating and/or impregnating material, e.g., against mold and insect contamination, contain an exactly determined amount of an organic and oil soluble lithium compound.

The wood preservative composition can be applied by painting, spraying, working pressure process, double vacuum processes, (a process under use of a double vacuum applied in two process stages), dipping and the like, however, preferably in a painting process.

The following examples are presented to further illustrate the present invention, it being understood that the examples are merely illustrative and not to be considered in a limiting sense.

EXAMPLE 1

The following is an example of a wood preservative priming composition:

| | |
|---|---|
| Pentachlorophenol | 5 wt. % |
| Lindane (γ hexachlorocyclohexane) | 0.5 wt. % |
| Alkyd resin (100%) | 15 wt. % |
| Siccative | 0.2 wt. % |
| Lithium naphthenate solution (dissolved in Spindle oil, Lithium content 2 wt. %) | 1 wt. % |
| Mineral oil, boiling range 170 to 220° C. | 78.3 wt. % |
| | 100.0 wt. % |

EXAMPLE 2

The following composition is for a wood-preservative, particularly one which is preventative for mold and insects and which is also combative against insects:

| | |
|---|---|
| Pentachlorophenol | 5 wt. % |
| Lindane (γ hexachlorocyclohexane) | 1 wt. % |
| Thiophosphoric acid ester | 1.5 wt. % |
| Phenolic acid ester | 1.5 wt. % |
| Phenolic resin | 4 wt. % |
| Tall oil ester | 5 wt. % |
| Lithium octoate solution in white spirits (Lithium content 2 wt. %) | 1 wt. % |
| Bitumen | 1 wt. % |
| White spirits - boiling range 170 to 220° C. | 81.5 wt. % |
| | 100.0 wt. % |

EXAMPLE 3

The following composition is for a wood-preservative, particularly one which is preventative for mold and insects and which is also combative against insects:

| | |
|---|---|
| Monochloronaphthaline | 50 wt. % |
| Spindle oil | 39.5 wt. % |
| Pentachlorophenol | 5 wt. % |
| Bitumen | 4 wt. % |
| Lindane (γ hexachlorocyclohexane) | 0.5 wt. % |
| Lithium naphthenate solution in Spindle oil; 2% Lithium | 1 wt. % |
| | 100.0 wt. % |

EXAMPLE 4

The following composition is for a wood-preservative, particularly one which is preventative for mold and insects and which is also combative against insects:

| | |
|---|---|
| Pentachlorophenol | 3 wt. % |
| Lindane (γ hexachlorocyclohexane) | 0.3 wt. % |
| Paraffins | 3 wt. % |
| Lithium naphthenate (in Spindle oil, 2 wt. % Lithium) | 60 wt. % |
| Balance: Spindle oil | 33.7 wt. % |
| | 100.0 wt. % |

What is claimed is:

1. In a preservative composition for wood, including an organic solvent base, at least one insecticide, an organic solvent base, at least one insecticide, organic fungicide or wood-preserving organic chemical compound which is soluble in said solvent, and a marking agent, the improvement which comprises said marking agent comprising at least one organic lithium compound soluble in said solvent, said organic lithium compound being present in an amount sufficient to permit a qualitative determination of the lithium in wood to which said composition is applied.

2. The preservative composition as defined by claim 1, wherein said solvent base comprises a difficulty volatile organic solvent having an evaporation number greater than 35 referred to diethylether and a flame point greater than 35 according to DIN 51 755.

3. The preservative composition as defined in claim 1, wherein said lithium compound is lithium naphthenate or lithium octoate.

4. The preservative composition as defined by claim 1, wherein said lithium compound is present in said composition in an amount of between about 0.005 and 0.1% by weight, calculated as metallic lithium and based upon said composition, whereby said lithium may be qualitatively and quantitatively determined in wood to which said composition is applied.

5. The preservative composition as defined by claim 4, wherein said lithium compound is present in said composition in an amount of between about 0.01 and 0.03% by weight, calculated as metallic lithium and based upon said composition, 6. The preservative composition as defined by claim 1, comprising:
 a. at least about 30% by weight of a difficultly volatile organic solvent having an evaporation number greater than 35 to diethylether and a flame point greater than 35; according to DIN 51 755;
 b. between about 0.5 and 20% by weight of at least one organic insecticide, organic fungicide or wood-preserving organic chemical compound; and
 c. between about 0.005 and 0.1% by weight, calculated as metallic lithium and based upon said composition, of an organic lithium compound soluble in said solvent.

7. The preservative composition as defined by claim 6, wherein said solvent has a flame point greater than 55 according to DIN 51 755 and is present in an amount of at least 50% weight, wherein said component b) is present in an amount of between about 2 and 10% by weight and wherein said lithium compound is present in an amount of between about 0.01 and 0.03% by weight.

8. The preservative composition as defined by claim 7, wherein said lithium compound is lithium naphthenate or lithium octoate.

9. The preservative composition as defined in claim 1, wherein said composition further comprises between about 1 and 20% by weight of a binder material.

10. The preservative composition as defined by claim 9, wherein said binder material is present in an amount of between about 4 and 15% by weight.

11. The preservative composition as defined in by claim 9, wherein said binder material is selected from the group consisting of a synthetic resin in the form of an emulsion, dispersion or solution and bitumen.

12. The preservative composition as defined in claim 11, wherein said synthetic resin is selected from the group consisting of an alkyd resin, a phenolic resin and an indene-cumarone resin.

13. The preservative composition as defined by claim 12, further comprising a plasticizer for said synthetic resin.

14. A method of treating wood with a wood preservative composition, comprising applying to the wood a composition as defined by claim 1, whereby the presence of said lithium in the wood provides qualitative evidence of treatment, a quantitative determination of the amount of lithium or calculation of the amount of preservative in the wood.

15. The method as defined by claim 14, wherein said solvent base of said composition comprises a difficultly volatile organic solvent having an evaporation number greater than 35 referred to diethylether and a flame point greater than 35 according to DIN 51 755.

16. The method as defined by claim 14, wherein said lithium compound is lithium naphthenate or lithium octoate.

17. The method as defined by claim 14, wherein said lithium compound is present in said composition in an amount of between about 0.005 and 0.1% by weight, calculated as metallic lithium and based upon said composition, whereby said lithium may be qualitatively and quantitatively determined in wood to which said composition is applied.

18. The method as defined by claim 17, wherein said lithium compound is present in said composition in an amount of between about 0.01 and 0.03% by weight, calculated as metallic lithium and based upon said composition.

19. The method as defined by claim 14, wherein said composition comprises
 a. at least about 30% by weight of a difficultly volatile organic solvent having an evaporation number greater than 35 referred to diethylether and a flame point greater than 35 according to DIN 51 755;
 b. between about 0.5 and 20% by weight of at least one organic insecticide, organic fungicide or wood-preserving organic chemical compound; and
 c. between about 0.005 and 0.1% by weight, calculated as metallic lithium and based upon said composition, of an organic lithium compound soluble in said solvent.

20. The method as defined by claim 19, wherein said solvent has a flame point greater than 55 according to DIN 51 755 and is present in an amount of at least 50% by weight, wherein said component b) is present in an amount of between about 2 and 10% by weight and wherein said lithium compound is present in an amount of between about 0.01 and 0.03% by weight.

21. The method as defined by claim 14, wherein said composition comprises an amount of said lithium compound sufficient to provide a wood-preserving effect.

22. The method as defined by claim 14, wherein said composition comprises between about 0.005 and 2% by weight, calculated as metallic lithium and based upon said composition.

23. The method as defined by claim 21, wherein said composition comprises between about 0.1 and 2% by weight, calculated as metallic lithium and based upon said composition.

24. The preservative composition as defined by claim 1, wherein said lithium compound is present in said composition in an amount of between about 0.005 and 2% by weight, calculated as metallic lithium and based upon said composition.

25. The preservative composition as defined by claim 1, wherein said solvent is selected from the group consisting of a mineral oil having a boiling range of between about 170° and 220° C., white spirits having a boiling range of from about 170° to 220° C., spindle oil having a boiling range of from about 250° to 350° C., kerosene, aromatics having the boiling range of from about 160° to 280° C. and oil of turpentine.

26. The preservative composition as defined by claim 1, wherein said lithium compound is selected from the group consisting of lithium naphthenate, lithium octoate, lithium acetate, lithium citrate, lithium glycerophosphate, lithium fumarate, lithium salicylate and lithium benzoate.

27. The preservative composition as defined by claim 1, wherein said insecticide, organic fungicide or wood-preserving organic chemical compound is selected from the group consisting of thio phosphoric acid esters, carbamates, pentachlorophenol, monochloronaphthalene and hexachlorocyclohexane.

28. The preservative composition as defined by claim 1, further comprising between about 0.5 and 5% by weight of a paraffin, a wax or wool grease as a water repellent agent.

29. The preservative composition as defined by claim 1 wherein said lithium compound is lithium octoate.

* * * * *